(12) United States Patent
Yamamichi

(10) Patent No.: US 7,863,051 B2
(45) Date of Patent: Jan. 4, 2011

(54) DETECTING ELEMENT AND DETECTION METHOD

(75) Inventor: Junta Yamamichi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 182 days.

(21) Appl. No.: 10/554,219

(22) PCT Filed: Jan. 18, 2005

(86) PCT No.: PCT/JP2005/000811

§ 371 (c)(1),
(2), (4) Date: Oct. 24, 2005

(87) PCT Pub. No.: WO2005/071393

PCT Pub. Date: Aug. 4, 2005

(65) Prior Publication Data

US 2006/0272433 A1 Dec. 7, 2006

(30) Foreign Application Priority Data

Jan. 23, 2004 (JP) .............................. 2004-015974

(51) Int. Cl.
*G01N 21/00* (2006.01)
(52) U.S. Cl. .................. 436/164; 436/172; 436/174; 436/177; 436/179; 436/180; 422/82.01; 422/100; 422/101; 422/102
(58) Field of Classification Search ............. 422/68.1, 422/82.01, 100–102; 436/63, 86, 149, 150, 436/174, 177, 179, 180, 164, 172
See application file for complete search history.

(56) References Cited

U.S. PATENT DOCUMENTS 6,267,858 B1 * 7/2001 Parce et al. ................. 204/600
6,294,392 B1   9/2001 Kuhr et al. .................. 436/518
6,454,945 B1 * 9/2002 Weigl et al. ................. 210/634
6,506,609 B1 * 1/2003 Wada et al. ................. 436/148

(Continued)

FOREIGN PATENT DOCUMENTS

JP      11-83784       3/1999

(Continued)

OTHER PUBLICATIONS

Joël S. Rossier, et al., "Enzyme Linked Immunosorbent Assay on a Microchip with Electrochemical Detection", Lab on a Chip, The Royal Society of Chemistry, vol. 1, No. 2, pp. 153-157 (2001).

(Continued)

*Primary Examiner*—Jill Warden
*Assistant Examiner*—Dwayne K Handy
(74) *Attorney, Agent, or Firm*—Fitzpatrick, Cella, Harper & Scinto

(57) ABSTRACT

A detection method for detecting a plurality of different substances contained in a specimen using a label, includes sequentially the steps of flowing the specimen through a detecting element having a first substance trapping portion immobilizing a first substance trapping body, a second substance trapping portion immobilizing a second substance trapping body, and a channel, and flowing a solution containing the label through the first substance trapping portion immobilizing the first substance trapping body and the second substance trapping portion immobilizing the second substance trapping body. Additional steps include flowing a solution for generating a signal from the label through the first substance trapping portion immobilizing the label to thereby acquire a signal from, and flowing a solution for generating a signal from the label through the second substance trapping portion immobilizing the label to thereby acquire a signal.

3 Claims, 6 Drawing Sheets

U.S. PATENT DOCUMENTS

| | | |
|---|---|---|
| 6,632,655 B1 * | 10/2003 | Mehta et al. .................. 506/14 |
| 6,649,358 B1 * | 11/2003 | Parce et al. .................. 435/7.2 |
| 2002/0076714 A1 | 6/2002 | Kuhr et al. .................... 435/6 |

FOREIGN PATENT DOCUMENTS

| | | |
|---|---|---|
| JP | 2002-71620 | 3/2002 |
| JP | 2002-277478 | 9/2002 |
| JP | 2004-500549 | 1/2004 |
| WO | WO 99/17119 | 4/1999 |
| WO | WO 01/07653 | 2/2001 |
| WO | WO 01/07653 A1 | 2/2001 |

OTHER PUBLICATIONS

Kiichi Sato, et al., "Integration of Chemical and Biochemical Analysis Systems into a Glass Microchip", Analytical sciences, vol. 19, pp. 15-22 (Jan. 2003).

Yoshikuni Kikutani, et al., "Integrated Chemical Systems on Microchips for Analysis and Assay. Potential Future, Mobile High-Performance Detection System for Chemical Weapons", Pure Appl. Chem., vol. 74, No. 12, pp. 2299-2309 (2002).

Hanbin Mao, et al., "Design and Characterization of Immobilized Enzymes in Microfluidic Systems", Analytical Chemistry, vol. 74, No. 2, pp. 379-385 (Jan. 15, 2002).

Kenichi Kojima, et al., "Electrochemical Protein Chip with Arrayed Immunosensors with Antibodies Immobilized in a Plasma-Polymerized Film", Analytical Chemistry, vol. 75, No. 5, pp. 1116-1122 (Mar. 1, 2003).

Notification of Reason for Refusal, translation of Japanese Office Action issued Apr. 18, 2007, in corresponding Japanese patent application No. 2004-015974.

* cited by examiner

DETECTING ELEMENT AND DETECTION METHOD

TECHNICAL FIELD

The present invention relates to a detecting element and a detection method. More specifically, the present invention relates to a detecting element and a detection method employing a plurality of layers of flow of a fluid in a microchannel, for detecting a plurality of different substances in a specimen.

BACKGROUND ART

An electrochemical technique is simple and costs little, and thus has been widely used as a biosensor using a product of a catalytic reaction such as a product of an enzymatic reaction. Recently, an array-type sensor provided with a plurality of microelectrodes has been developed with miniaturization of electrodes in a detecting unit (see Japanese Patent Application Laid-Open No. 2002-071620).

An array-type sensor is capable of acquiring two-dimensional positional information with respect to the same specimen and dynamic changes in substance distribution. Further, an array-type sensor may perform multichannel detection through reactions of electrodes set in array with specific, different specimens (See Kenichi Kojima, Atsunori Hiratsuka, Hiroaki Suzuki, Kazuyoshi Yano, Kazunori Ikebukuro, and Isao Karube, "Analytical Chemistry" 2003, 75, p. 1116-1122).

Meanwhile, a measuring device for sampling and measuring in a microchannel is used as a microfluidic device. Niwa et al. have proposed an online biosensor including a microchannel and a thin layer channel in combination and have conducted a continuous quantitative analysis of a trace amount of a sample (Japanese Patent Application Laid-Open No. H11-083784).

However, those techniques alone hardly allow separation and detection of a plurality of detection target substances in an actual measurement sample (such as blood) in the same channel at the same time. For example, the measurement sample may be distributed to a plurality of channels to detect the detection target substances in the respective channels, but a required amount of the measurement sample increases. In the case where a trapping site for trapping a plurality of detection target substances in the specimen is provided in a channel, a reaction product of a catalytic reaction, which is derived from the detection target substances with a catalyst, is often the same substance for some of the detection target substances. The product of a catalytic reaction diffuses in a liquid, and thus, from which detection target substance the product was produced was hardly identified with one detecting unit (such as an electrode).

DISCLOSURE OF THE INVENTION

The present invention has been made in view of the prior art, and an object of the present invention is therefore to provide a detecting element and a detection method capable of detecting efficiently and simultaneously a trace amount of a plurality of different substances in a specimen by: supplying a trace amount of the specimen containing a plurality of different substances into a substance trapping portion without dividing a channel of a detecting element employing the channel into a plurality of channels and without distributing the specimen thereinto; and forming in the channel a plurality of substance trapping portions having respectively different detection targets.

A first aspect of the present invention relates to a detecting element for detecting a plurality of different substances in a specimen, characterized by including: a channel provided on a substrate, which is capable of forming a plurality of layers of flow of a fluid; and a plurality of different substance trapping portions provided in the channel, for trapping the plurality of different substances in the specimen, respectively, in which: the plurality of different substance trapping portions are provided separately in accordance with the plurality of layers of flow of a fluid to be formed; and the plurality of different substance trapping portions are each arranged to acquire independent information on each of the substances in the specimen through an action between the fluid and the trapped substance.

The detecting element preferably further includes a detecting unit for detecting the information.

The plurality of different substances in the specimen each preferably have a label, and the fluid flowing along the plurality of layers of flow is preferably a fluid acting on the label to discharge an active product.

The label is preferably a substance having a catalytic action, a substance having electrochemiluminescence, or a fluorescent substance.

A second aspect of the present invention relates to a detection method for detecting a plurality of different substances in a specimen, characterized by including the steps of: introducing the specimen into a channel having a plurality of different substance trapping portions for specifically trapping the plurality of different substances, respectively, to trap the substances in the substance trapping portions; forming a plurality of layers of flow of a fluid in the channel; and switching and passing the fluid forming the plurality of layers of flow, to acquire independent information on each of the substances in the specimen through an action between the fluid and the trapped substance.

The present invention provides a detecting element and a detection method capable of detecting efficiently and simultaneously a trace amount of a plurality of different substances in a specimen by: supplying a trace amount of the specimen containing a plurality of different substances into a substance trapping portion without dividing a channel of a detecting element employing the channel into a plurality of channels and without distributing the specimen thereinto; and forming in the channel a plurality of substance trapping portions having respectively different detection targets.

Figure 1:
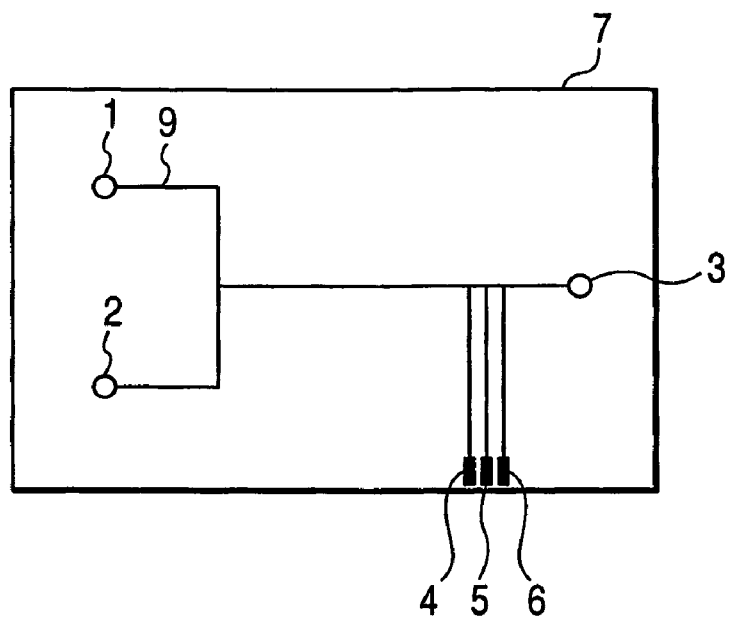
FIG. 1 is a schematic diagram showing an example of a structure of a biosensor according to the present invention.

The reference numerals used in the drawings indicate the following portions:

1, 2 inlet
3 drain
4, 5, 6 electrode pad
7 substrate
9 microchannel
10, 11 substance trapping portion
13 PDMS substrate
14 microchannel
15 glass substrate
16, 17, 18 thin film electrode
19, 20, 21 electrode pad
22, 23, 24 through hole
25 PDMS substrate
26 BSA
27 rabbit antibody to AFP
28 AFP
29 mouse antibode to AFP
30 goat antimouse antibody
31 GOX
32, 33, 34 electrode pad
35 microchannel
36, 37, 38 inlet
39 drain
40 substrate
42, 43 substance trapping portion
44, 45 interface
46 subjected to hydrophobic treatment
47 substrate
48 microchannel
49 glass substrate
50, 51, 52, 53 through hole
54 PDMS substrate
55 BSA
56 rabbit antibody to AFP
57 AFP
58 mouse antibody to AFP
59 goat antimouse antibody
60 HRP
71, 72 laminar flow

BEST MODE FOR CARRYING OUT THE INVENTION

Hereinafter, the present invention will be described in detail.

A detecting element of the present invention is a detecting element for detecting a plurality of different substances in a specimen, characterized by including: a channel provided on a substrate, which is capable of forming a plurality of layers of flow (hereinafter, referred to as laminar flows) of a fluid; and a plurality of different substance trapping portions provided in the channel, for trapping the plurality of different substances in the specimen, respectively, in which the plurality of different substance trapping portions are each arranged to acquire independent information on each of the substances in the specimen by switching the fluid forming the plurality of laminar flows.

Further, a detection method of the present invention is a detection method for detecting a plurality of different substances in a specimen, characterized by including the steps of: introducing the specimen into a channel having a plurality of different substance trapping portions for specifically trapping the plurality of different substances; forming a plurality of laminar flows in the channel; and switching the fluid forming the plurality of laminar flows, to acquire independent information on each of the substances in the specimen.

Figure 2:
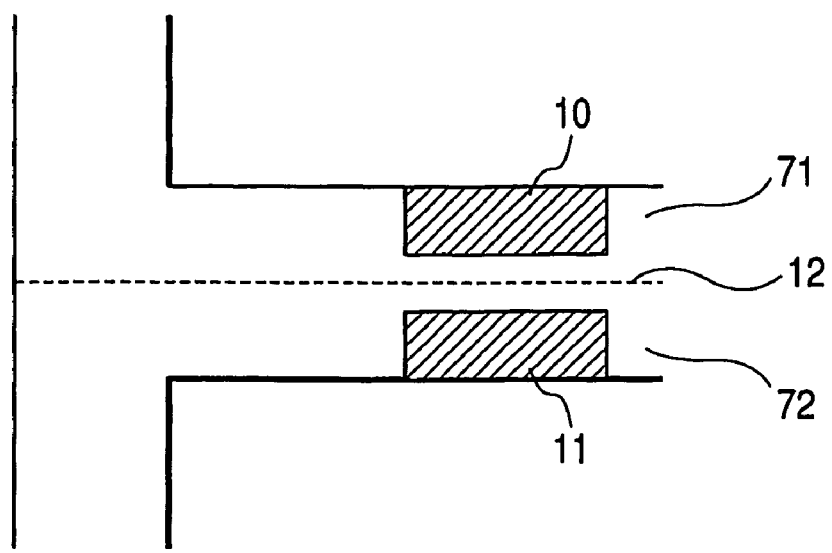
FIG. 2 is a schematic diagram showing substance trapping portions in a microchannel of Example 1.

A general mode of the present invention is a detecting element of a µTAS (Micro Total Analysis Systems) type represented in FIG. 1. As shown in FIG. 2, an antibody bonding specifically with a substance in a specimen is immobilized onto a substance trapping portion in the microchannel.

A plurality of substance trapping portions are formed in the channel to trap a plurality of substances in the specimen, respectively.

The substance trapping portions are each arranged to acquire independent information on each of the substances by switching a fluid forming a plurality of laminar flows in the channel. The fluid forming the laminar flows is switched for acting on a label of a substance in the specimen to pass a fluid (substrate) for discharging an active product through one layer alone, and the discharged active product is detected, to thereby acquire information such as an amount of the substance in the specimen trapped in the substance trapping portion corresponding to the layer.

Examples of the label that can be used include a substance having a catalytic action, a substance having electrochemiluminescence, and a fluorescent substance. Further, a substance itself in the specimen may serve as a label. A substance in the specimen is detected by, for example: forming a complex of the specimen trapped in the substance trapping portions and an enzyme-labeled, substance-specific secondary antibody; selectively supplying an enzyme-substrate acting on the enzyme-label with a fluid forming laminar flows corresponding to the respective substance trapping portions; and detecting the produced enzymatic reaction product (active product) with a detecting electrode provided downstream of the substance trapping portions.

A target specimen may be one which can be specifically recognized by an antibody of a biological substance (protein, nucleic acid, sugar chain), allergen, bacteria, virus, or the like.

The complex to be formed in the substance trapping portions may include a tertiary or higher enzyme-labeled antibody which specifically bonds with a complex of the specimen and the secondary antibody, in addition to the enzyme-labeled secondary antibody.

Further, in the case where a fluorescent substance is used as a labeling substance, selective detection involves changing of pH of the laminar flows and selective spectrum shifting.

Examples of the substance having a catalytic action include glucose oxidase, choline oxidase, lactose oxidase, and horseradish peroxidase. Examples of a substrate therefor include glucose, choline, lactose, luminol, and hydrogen peroxide. An example of the substance having electrochemiluminescence includes tris(bipyridyl)ruthenium. Examples of the fluorescent substance include: 5-carboxyfluorescein; 8-amino-2-(trans-2-aminostyryl)-6-methoxyquinoline-N,N,N',N'-tetraacetic acid, tetrasodium salt (Quene-1); and 2',7'-bis(carboxyethyl)-4(5)-carboxyfluorescein (BCECF).

The detecting element of the present invention allows integration of the substance trapping portions for detecting a plurality of substances in the specimen, and efficient detection of the specimen with a smaller amount. Further, the specimen need not be divided and passed through multichannels, and the specimen can be used as efficiently as possible.

Further, in a biosensor, the detection method allows selective detection of signals (enzymatic reaction product, chemiluminescence, and fluorescence) from the respective substance trapping portions. Specific detecting units for the respective reactions are not required, and the detecting units can be shared. The detection method allows integration and sharing of the substance trapping portions and the detecting units, to thereby provide a microsensor at low cost.

Hereinafter, the present invention will be described in more detail based on examples with reference to drawings. However, the present invention is not limited to the following examples.

EXAMPLE 1

FIG. 1 shows a structure of a biosensor according to an embodiment of the present invention. Glucose oxidase (GOX) was used as a substance having a catalytic action. Further, human α-fetoprotein (AFP) and human β2-microglobulin (β2MG) were used as specimens of measuring objects.

Figure 3:
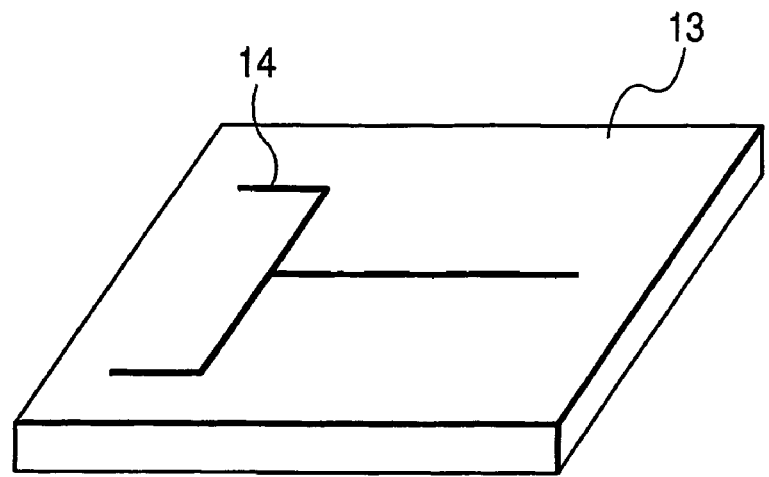
FIG. 3 is a schematic diagram showing a constitution of a PDMS substrate of Example 1.
Figure 4:
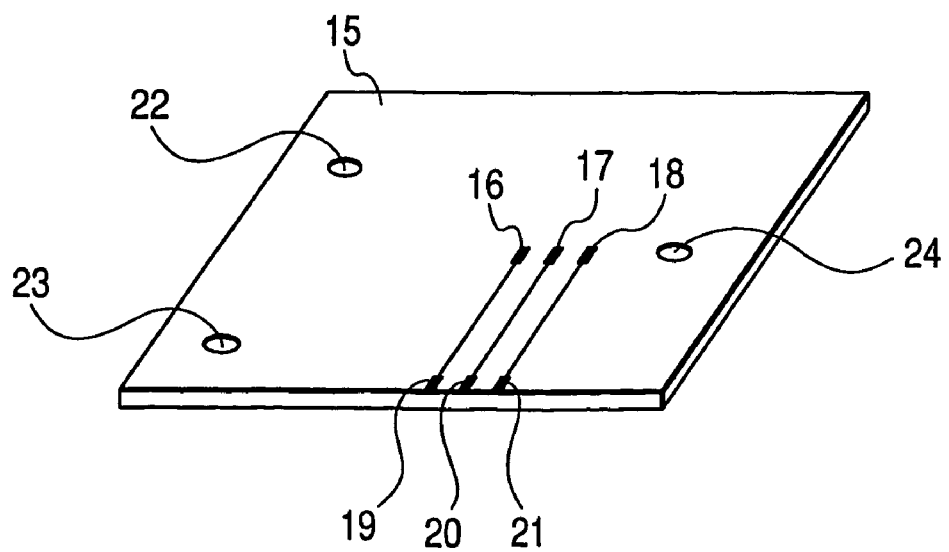
FIG. 4 is a schematic diagram showing a constitution of a glass substrate of Example 1.

The biosensor had a structure including a polydimethylsiloxane (PDMS) substrate and a glass substrate attached together. A rectangular microchannel 14 having a width of 100 μm and a depth of 100 μm was patterned on a PDMS substrate 13 (see FIG. 3). Thin film electrodes 16, 17, and 18 for detecting hydrogen peroxide and electrode pads 19, 20, and 21 were patterned on a glass substrate 15 (see FIG. 4). The electrodes and the electrode pads were formed by laminating titanium and platinum through sputtering in the described order. The glass substrate was provided with through holes (diameter of 100 μm) 22, 23, and 24 used as two inlets 1 and 2 for injecting a specimen and one drain 3. A reference electrode 17 was plated with silver as a reference material.

As shown in FIG. 2, substance trapping portions 10 and 11 were provided in a microchannel, and a rabbit antibody to human AFP and a rabbit antibody to human β2MG were cross-linked and immobilized on the substance trapping portions respectively with a glutaraldehyde vapor through bovine serum albumin (BSA). The PDMS substrate and the glass substrate were attached through autoadsorption. A phosphate buffered saline was used as a measuring solution, and was supplied from the two inlets 1 and 2 at a flow rate of 2 μl/min each by a syringe pump.

Figure 5:
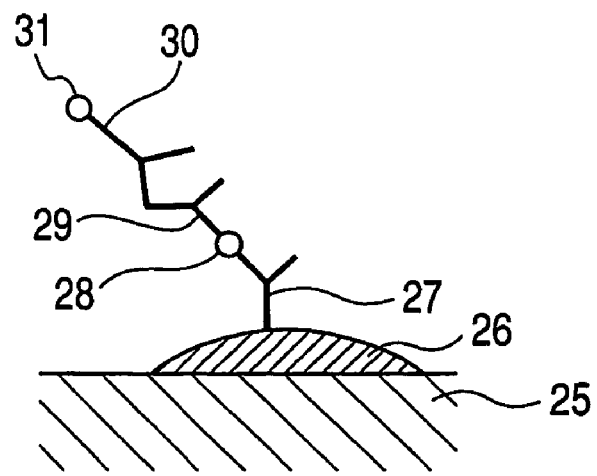
FIG. 5 is a schematic diagram of a reaction in the substance trapping portions of Example 1.
Figure 6:
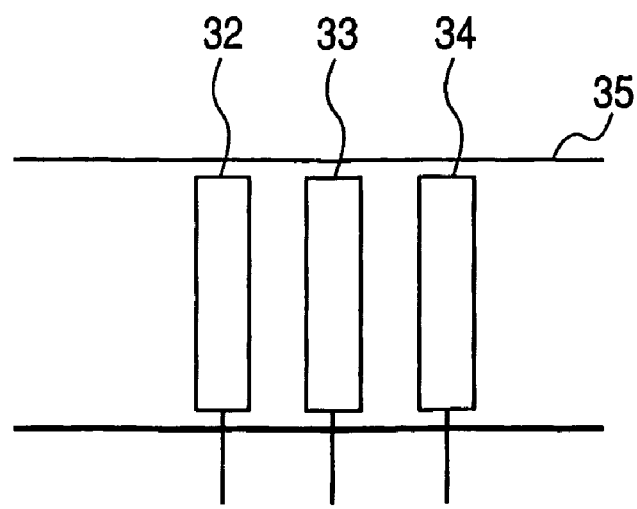
FIG. 6 is a schematic diagram of an electrode unit of Example 1.

Three electrode pads 32, 33, and 34 of a working electrode, a reference electrode, and a counter electrode aligned as shown in FIG. 6 were connected to terminals of a potentiostat, respectively. When a mixed solution of human AFP and human β2MG as a specimen was supplied as the measuring solution from the two inlets, human AFP and human β2MG were bonded to the substance trapping portions through the respective immobilized antibodies. Next, secondary antibodies (mouse-derived) to human AFP and to human β2MG were supplied thereto. Finally, a GOX-modified goat antimouse antibody was supplied thereto as a tertiary antibody, to thereby form a complex as shown in FIG. 5.

Then, the specimen was assayed. Human AFP and human β2MG were trapped separately in the microchannel. Laminar flows 71 and 72 were formed in the microchannel to pass glutamic acid which is a GOX enzyme-substrate through the respective substrate trapping portions. A buffer solution containing glutamic acid was passed through only one of the two inlets 1 and 2, to thereby detect hydrogen peroxide generated from only one GOX of AFP trapping portion and β2MG trapping portion as a reduction current by using the thin film electrodes 16, 17, and 18 provided downstream. Then, an inlet for introducing glutamic acid was switched, to thereby detect hydrogen peroxide generated from a different GOX. Such an operation allows separate detection of two specimens (AFP and β2MG) trapped in one microchannel using the same label with one detecting unit.

EXAMPLE 2

Figure 7:
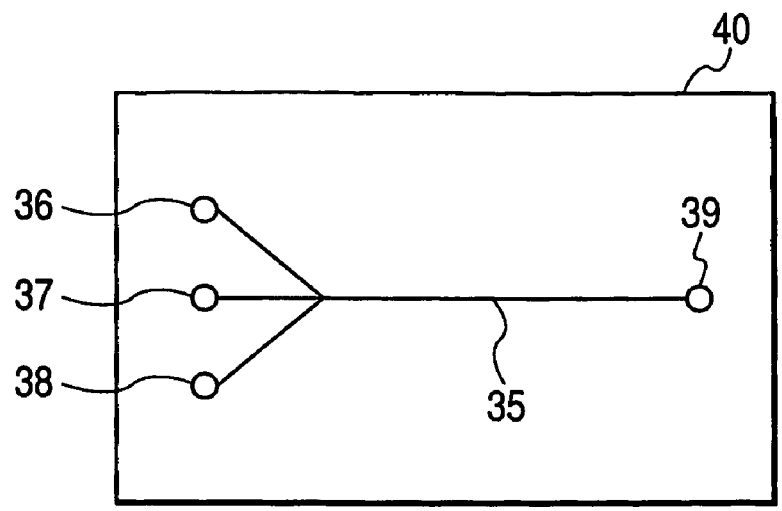
FIG. 7 is a schematic diagram showing a structure of a biosensor shown in Example 2.
Figure 9:
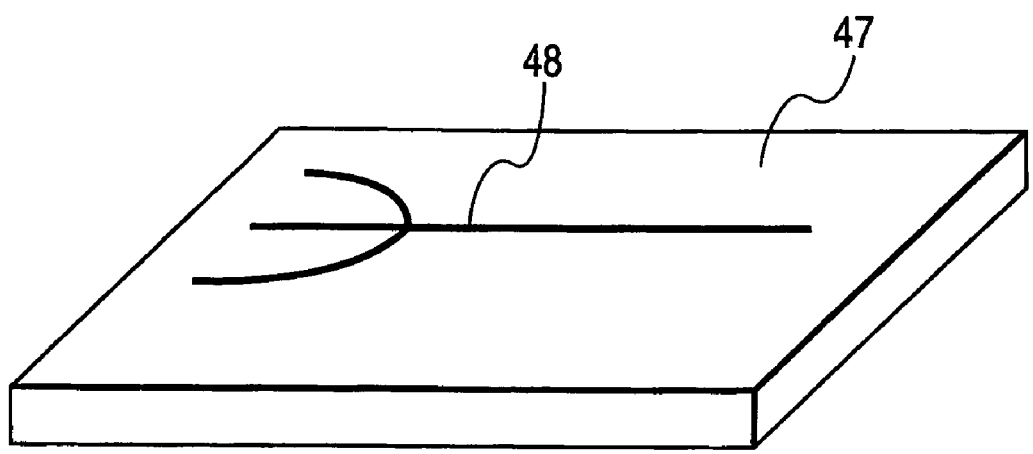
FIG. 9 is a schematic diagram showing a constitution of a microchannel on a glass substrate of Example 2.

A biosensor having a structure as shown in FIG. 7 was prepared. A glass substrate was used as a substrate. As shown in FIG. 9, a microchannel 48 having a width of 100 μm and a depth of 50 μm was formed on a glass substrate 47 through a wet etching process. The laminar flows formed in Example 1 were detected more strictly, to thereby suppress diffusion of the substrate and form substance trapping portions more closely. In this way, the substance trapping portions can be formed at higher density.

Figure 8:
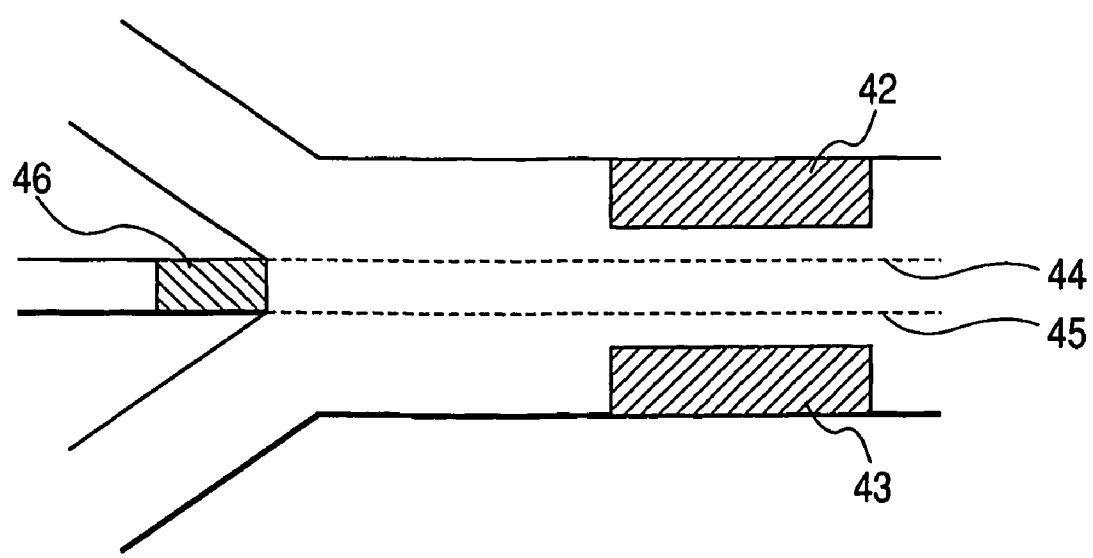
FIG. 8 is a schematic diagram of substance trapping portions in a microchannel of Example 2.

In this example, three inlets were formed as shown in FIG. 8. A central inlet passed a solution used for detecting laminar flows more strictly. Thus, an organic solution is more desirable than an aqueous solution. In this example, ethanol was used. A surface of a microchannel connected to the central inlet was subjected to hydrophobic treatment just before a convergence 46 with other two channels, to thereby prevent backflow of a phosphate buffered saline flowing from the other two inlets. A fluorine compound ($CF_3(CF_2)_7CH_2CH_2Si(OMe)_3$) was used for the hydrophobic treatment and was coated onto the surface. Horseradish peroxidase (HRP) was used as a labeling enzyme.

Figure 10:
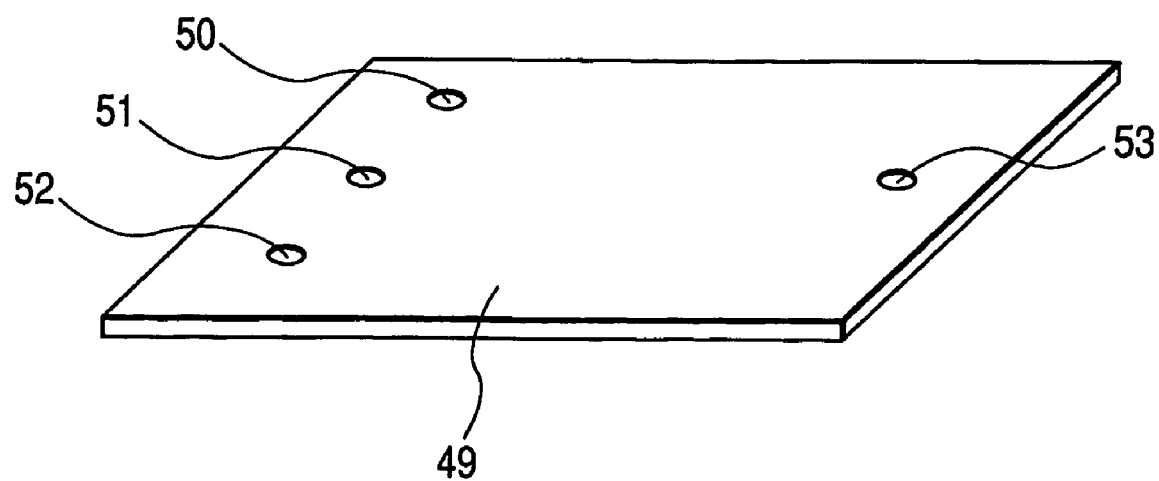
FIG. 10 is a schematic diagram showing a constitution of through holes on the glass substrate of Example 2.
Figure 11:
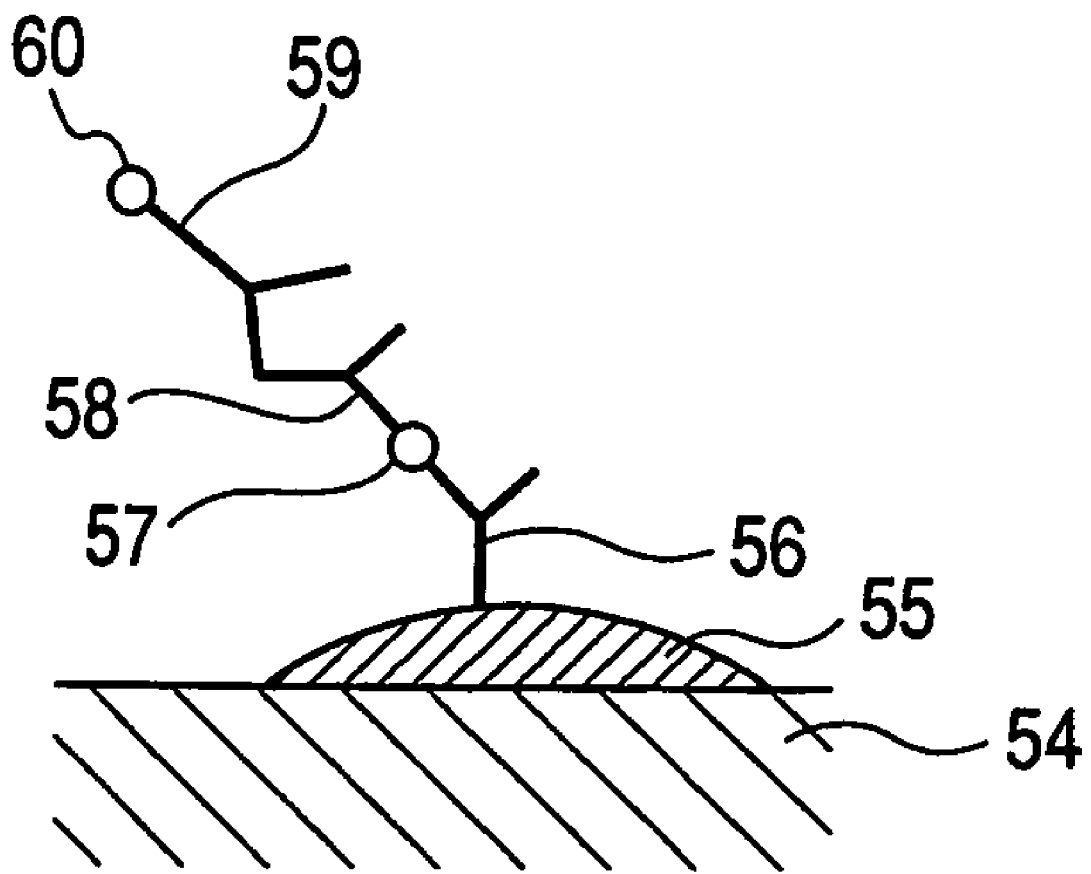
FIG. 11 is a schematic diagram of a reaction in the substance trapping portions of Example 2.

Similar to Example 1, primary antibodies were immobilized on substance trapping portions 42 and 43 of FIG. 8. As shown in FIG. 10, through holes 50, 51, 52, and 53 for the inlets and a drain were formed on the glass substrate. The two glass substrates were attached together with an ultraviolet curing adhesive by masking a microchannel portion to prevent ultraviolet exposure thereto. In the measurement of the specimen, a mixed solution of human AFP and human β2MG was supplied from inlets 36 and 38 at a flow rate of 2 μl/min by a syringe pump. Next, secondary antibodies (mouse-derived) to human AFP and human β2MG were supplied thereto. Finally, an HPR-modified goat antimouse antibody was supplied thereto as a tertiary antibody, to thereby form a complex as shown in FIG. 11.

Then, the specimen was assayed. Human AFP and human β2MG were trapped separately in the microchannel. Laminar flows were formed in the microchannel to pass luminol which is an HRP enzyme-substrate through the respective substance trapping portions 42 and 43. A phosphate buffered saline containing luminol and hydrogen peroxide was passed through only one of the two inlets 36 and 38. A phosphate buffered saline was passed through the other inlet. Further, ethanol was passed through the inlet 37 to separate two water phases and reduce diffusion of luminol. Luminol and hydrogen peroxide reacted through a catalytic action of HRP, to thereby form a 3-aminophthalate dianion and, at the same time, cause chemiluminescence. The specimen bonded to the substance trapping portion 42 or 43 was assayed by measuring a luminescence intensity.

Then, an inlet for introducing luminol and hydrogen peroxide was switched, to thereby detect chemiluminescence by different HRP. Such a procedure allows separate detection of two specimens (AFP and β2MG) trapped in one microchannel using the same label.

EXAMPLE 3

A fluorescent label can be used in place of the enzyme-label in the systems of Examples 1 and 2.

A pH of a fluid in a specific layer was changed by formation of laminar flows to change fluorescent characteristics of the fluorescent label, to thereby allow distinction of the specimens. The specimens were distinguished by detecting fluorescence intensities at a specific wavelength or changes in fluorescence spectra. Similar to Example 2, the specimen can be detected by using pH-sensitive fluorescent dye 5-carboxyfluorescein as a label for a tertiary antibody.

INDUSTRIAL APPLICABILITY

The detecting element and detection method of the present invention allow efficient and simultaneous detection of a trace amount of a plurality of substances in a specimen, and thus can be used for a biosensor for medical diagnoses, medical examinations, food safety inspections, environmental pollutant tests, or the like.

This application claims priority from Japanese Patent Application No. 2004-015974 filed Jan. 23, 2004, which is hereby incorporated by reference herein.

The invention claimed is:

1. A detection method for detecting a plurality of different substances contained in a specimen using a same label, comprising sequentially the steps of:

flowing the specimen having a first substance and a second substance through a detecting element having a first substance trapping portion immobilizing a first substance trapping body for specifically trapping and immobilizing the first substance contained in the specimen, a second substance trapping portion immobilizing a second substance trapping body for specifically trapping and immobilizing the second substance contained in the specimen, the second substance being different from the first substance, and a channel, with the first substance trapping portion being different than the second substance trapping portion;

flowing a solution containing the label through the first substance trapping portion immobilizing the first substance trapping body and the second substance trapping portion immobilizing the second substance trapping body, the label comprising a first group of label molecules bonded with a third substance trapping body capable of specifically acting on the first substance and a second group of label molecules bonded with a fourth substance trapping body capable of specifically acting on the second substance;

flowing a solution for generating a signal from the label through the first substance trapping portion immobilizing the label such that a first layer of aqueous solution flow through the first substance trapping portion and a second layer of aqueous solution flow through the second substance trapping portion coexist while a third layer of alcoholic solution flow exists between the first layer of aqueous solution flow and the second layer of aqueous solution flow and that the solution for generating a signal from the label forms the first layer of aqueous solution flow, to thereby acquire a signal from the first substance trapping portion; and flowing a solution for generating a signal from the label through the second substance trapping portion immobilizing the label such that a first layer of aqueous solution flow through the first substance trapping portion and a second layer of aqueous solution flow through the second substance trapping portion coexist while a third layer of alcoholic solution flow exists between the first layer of aqueous solution flow and the second layer of aqueous solution flow and that the solution for generating a signal from the label forms the second layer of aqueous solution flow, to thereby acquire a signal from the second substance trapping portion.

2. A detection method according to claim 1, wherein the label is an enzyme and the solution for generating a signal from the label is a solution containing a substrate for the enzyme.

3. A detection method according to claim 1, wherein the label is pH-sensitive fluorescent dye and the solution for generating a signal from the label is a solution having a pH which changes a fluorescent characteristic of the pH-sensitive fluorescent dye.

* * * * *